United States Patent [19]

Hansen et al.

[11] Patent Number: 5,523,055
[45] Date of Patent: Jun. 4, 1996

[54] FLUID SPECIMEN COLLECTION AND TESTING APPARATUS

[76] Inventors: Warren D. Hansen, 8378 Azul Way; Richard H. Taylor, 1892 E. Brady Creek Dr., both of Sandy, Utah 84093; Bobbye J. Wetsel, 13278 S. Jared Cir., Riverton, Utah 84065

[21] Appl. No.: 295,998

[22] Filed: Aug. 24, 1994

Related U.S. Application Data

[62] Division of Ser. No. 72,592, Jun. 3, 1993, Pat. No. 5,352,410.

[51] Int. Cl.$^6$ .................................................. G01N 21/00
[52] U.S. Cl. ........................ 422/58; 422/61; 422/102; 422/101; 436/808
[58] Field of Search ............................ 422/56–58, 61, 422/102, 101; 436/808

[56] References Cited

U.S. PATENT DOCUMENTS

| | | | |
|---|---|---|---|
| 4,315,890 | 2/1982 | Tamers | 422/61 |
| 4,376,634 | 3/1983 | Prior et al. | 436/502 |
| 4,791,060 | 12/1988 | Chandler | 422/61 |
| 4,865,813 | 9/1989 | Leon | 422/61 |
| 5,133,470 | 7/1992 | Abrams et al. | 215/250 |
| 5,160,329 | 11/1992 | Oxley | 604/317 |

Primary Examiner—Lyle A. Alexander
Attorney, Agent, or Firm—Daniel McCarthy

[57] ABSTRACT

A device for the collection and testing of a fluid specimen is disclosed and claimed. The invention is particularly useful for collecting and testing human urine specimens but may also be employed in the veterinary environment or any time a potentially hazardous fluid is to be collected and tested and isolation of the specimen from testing personnel is desired. The invention keeps the specimen enclosed and sealed during transport and testing to facilitate safe handling of specimen. Some embodiments of the invention are highly resistant to tampering by the patient or during transport.

12 Claims, 9 Drawing Sheets

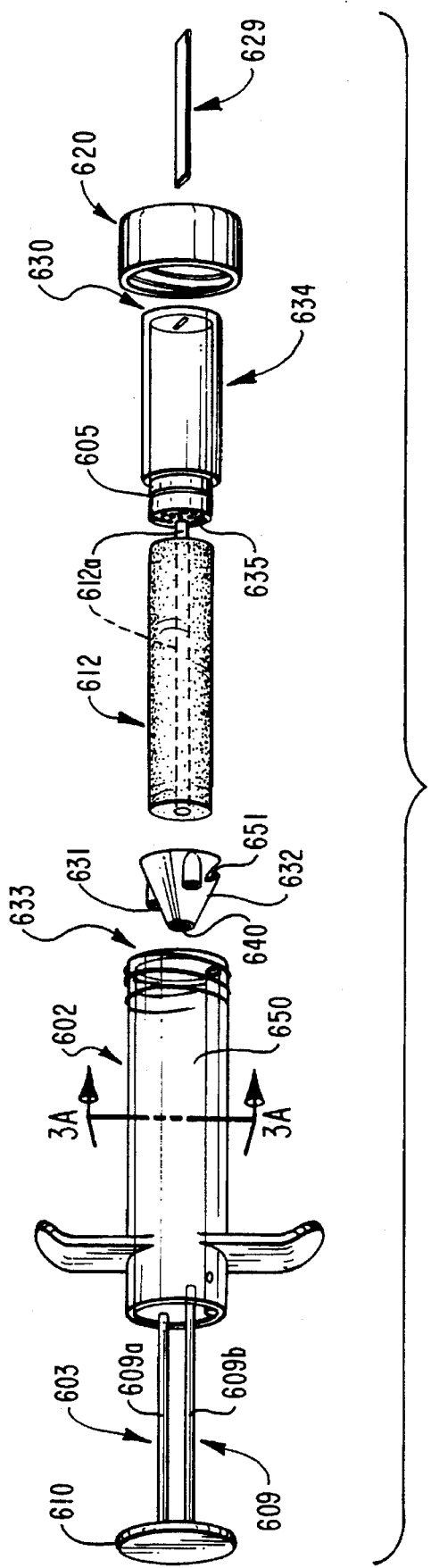
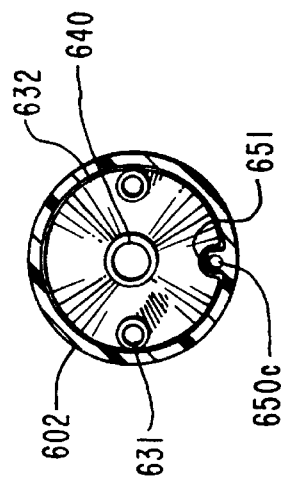
FIG. 3
FIG. 3A

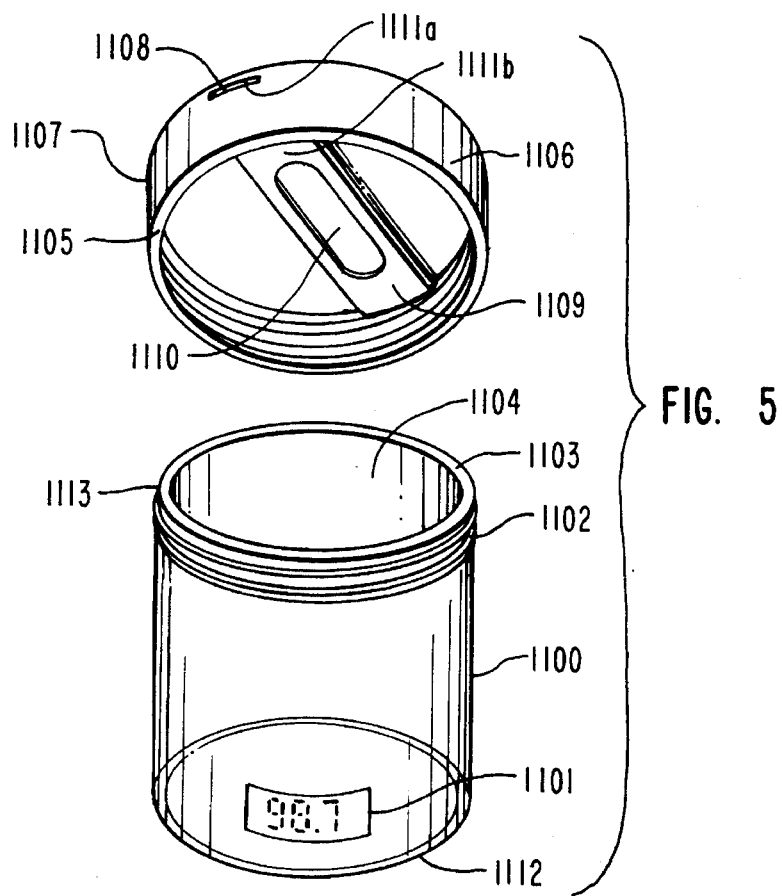
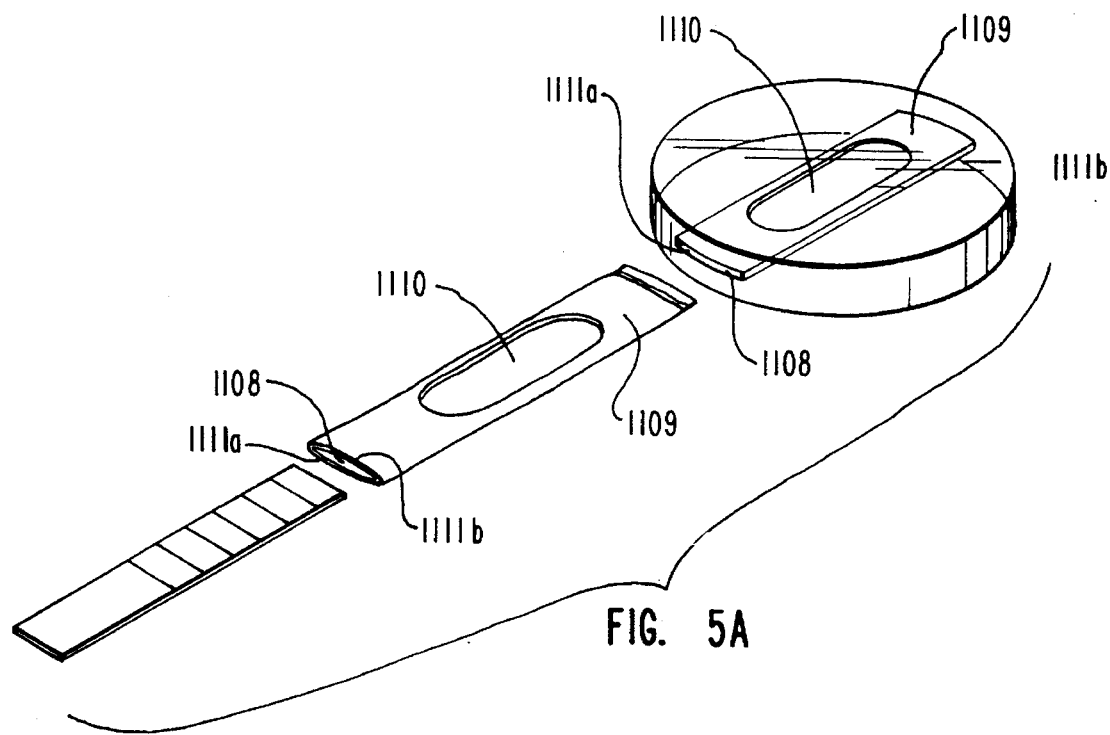
FIG. 5
FIG. 5A

FLUID SPECIMEN COLLECTION AND TESTING APPARATUS

BACKGROUND OF THE INVENTION

This application is a divisional of application Ser. No. 08/072,592 which was filed on Jun. 3, 1993 now U.S. Pat. No. 5,352,410, and priority is claimed thereto. Be it known that WARREN D. HANSEN, PH.D., RICHARD H. TAYLOR, M.D., and BOBBYE JO WETSEL, R.N., citizens of the United States of America and residents of the state of Utah have invented a new and useful invention entitled "FLUID SPECIMEN COLLECTION AND TESTING APPARATUS" of which the following comprises a complete specification.

A. Field of Invention

The invention relates to the field of devices used for the collection and testing of a fluid specimen. The invention is particularly useful for collecting and testing biological fluid specimens, including human urine specimens. Other fluid specimens, such as biological fluid specimens in a veterinary setting or effluent samples in an industrial environment may also be collected and tested. The invention can be used to absorb a fluid specimen, seal it in a container or enclosure so that contact with persons transporting, handling or testing the specimen is prevented, subject the specimen to one or more tests which may include further transportation of the specimen, and disposal of the specimen sealed within the container or enclosure. The invention is highly resistant to tampering by the patient or during transport, and provides substantial advances in the safe handling of biological fluid specimens by medical personnel.

B. The Background Art

The typical biological fluid specimen collection and testing device used in the prior art consists of an open container, such as a cup, into which a patient places a biological fluid specimen, such as urine. The container may include a temperature indicator to aid in detection of a false specimen such as tap water, stored urine, or other fluids. If a fluid specimen with a temperature substantially greater than or less than normal body temperature, such as tap water, is placed into the container, then testing personnel could readily observe a suspicious temperature reading. After the patient has placed a specimen in the container, a cover is placed onto the container and the container is handed or transported to medical personnel, such as a nurse. The nurse then uncovers the container and dips various reagent strips into the specimen to test for the presence of controlled substances and to test for various medical conditions, such a diabetes. The specimen may be subjected to further testing procedure as needed. After testing of the specimen is complete, medical personnel typically pour the specimen down a drain and place the used container into a trash receptacle. In other industries, such as chemical manufacturing or environmental remediation, open containers are also used for collection of fluid specimens for testing.

A very important disadvantage of the prior art device is that it exposes the nurse and other persons to a high risk of contact with the specimen. In order to test the specimen, the nurse must remove the cover of the container. Uncovering the container sometimes results in spilling, splashing, dripping or leaking the specimen from the container, at times resulting in the nurse or other persons experiencing direct physical contact with the specimen. When the specimen is being tested, typically by dipping reagent strips into the specimen, the nurse is in very close physical proximity to the specimen, causing a substantial danger of spilling, splashing, dripping or leaking the specimen from the container, possibly resulting in direct physical contact between the nurse and the specimen. When testing of the specimen is complete and the nurse disposes of the specimen and container by pouring the specimen down a drain and placing the container into a trash receptacle, there is again the danger of spilling, splashing, dripping or leaking the specimen from the container and causing it to come into direct physical contact with the nurse or other persons.

Current awareness of and concern regarding communicable diseases such as hepatitis and the virus causing acquired immune deficiency syndrome (AIDS) makes the danger of contact between specimen and medical personnel very undesirable. The prior art fluid specimen collection container did little to mitigate this danger. The chance of contact between medical personnel and specimen is magnified for medical personnel who perform many specimen testing operations daily. Specimen testing is considered a hazardous and undesirable occupation due to the possibility of contracting a deadly disease. This can give rise to poor worker morale, the necessity of paying higher wages to specimen testing personnel, increased insurance costs, and the possibility of employer liability if specimen testing personnel are infected by contact with specimen.

Another important disadvantage of the prior art device is that keeping the specimen in an open container allows odors emitting from the specimen to escape into the ambient air. Although odor is not viewed as being as dangerous to medical personnel as direct physical contact with specimen, it is offensive to the senses and creates an unpleasant work environment.

Another disadvantage of the typical biological fluid collection and testing device used in the prior art is that it is subject to tampering such as specimen alteration or replacement, during transport from the specimen collection site to the specimen testing site. The cover of the typical prior art fluid collection device may easily be removed and the specimen altered or replaced. A disadvantage of the typical prior art fluid specimen collection device used in other industries, such as chemical manufacturing or environmental remediation, is that specimen collection and testing personnel are in danger of contact with specimen which may contain chemicals or other hazardous substances, and there is a danger of spilling some specimen and causing both health hazards and environmental contamination.

The medical industry has responded to some of the disadvantages of the prior art specimen collection and testing device by constructing tamper-proof containers from which a specimen cannot be removed or into which additional material may not be placed without visual evidence of tampering. An example of such a device is U.S. Pat. No. 5,133,470 issued to Abrams et al. Such tamper-proof containers, while partially effective in avoiding specimen tampering, offer no features to protect medical testing personnel from the possibility of direct physical contact with the specimen.

Another response by the medical industry to the disadvantages of the prior art specimen collection and testing device is U.S. Pat. No. 5,160,329 issued to Oxley. Oxley discloses a multi-compartment fluid specimen collection bag. Oxley's multi-compartment design is intended to capture multiple redundant specimen samples for various tests. The Oxley invention is unwieldy to use due to the necessity of providing a holder for the bag when the patient places a specimen into the bag. Oxley is also bulky and difficult to handle, both for the patient and for medical personnel. Oxley also requires a substantial volume of specimen in order to provide sufficient redundant specimen samples for multiple tests. Finally, due to the size and complexity of the Oxley invention, the cost of manufacture is too high to make it practical in high volume specimen testing settings.

II. SUMMARY OF THE INVENTION

It is an object of the invention to provide a fluid specimen collection and testing apparatus. All embodiments of the invention provide a means for collecting a fluid specimen, a means for sealing a fluid specimen within a container, and a means for testing a fluid specimen.

It is an object of the invention to provide a sealable specimen collection and testing apparatus. The invention includes features which allow the specimen to be sealed in fluid confinement within the apparatus to prevent physical contact with the specimen by medical personnel.

It is an object of the invention to provide a tamper-proof fluid specimen collection and testing apparatus. The invention provides a fluid specimen collection and testing apparatus which may be sealed upon collection of the fluid specimen, and may not thereafter be unsealed or opened without substantial damage to or destruction of the apparatus. This feature virtually precludes tampering with specimen after collection because any such tampering would be readily apparent.

Another object of the invention is to provide a self-contained fluid specimen collection and testing apparatus. Several embodiments of the invention contain all parts necessary to collect, contain, test and dispose of a fluid specimen without the use of any accessories or other devices.

Another object of the invention is to provide a disposable fluid specimen collection and testing apparatus. The invention utilizes simple design features and inexpensive components which make disposal of the collection and testing apparatus immediately after testing is completed economically feasible.

Another object of the invention is to provide a fluid specimen collection and testing apparatus from which specimen does not exit once placed therein by the patient. Several embodiments of the invention provide a specimen collection and testing apparatus which permanently seals the specimen in fluid confinement within the interior of the apparatus, preventing the escape of specimen from the apparatus short of destruction of the apparatus. This feature also facilitates joint disposal of the specimen and apparatus rather than separate disposal as found in the prior art.

Another object of the invention is to provide a permanent sealed barrier between specimen and medical personnel to eliminate the possibility of direct physical contact between medical personnel and the specimen. Several embodiments of the invention permanently seal the specimen within the interior of the collection and testing apparatus such that the apparatus acts as a barrier between medical personnel and specimen, preventing any physical contact between medical personnel and specimen. This feature of the invention results in a substantial decrease in the danger of disease to medical personnel who handle and test specimens with the invention. Added safety provided when the invention is used may result in better worker morale, lower insurance costs, and less likelihood of employer liability due to exposure of medical personnel to specimens which may carry dangerous diseases.

Another object of the invention is to provide a fluid specimen collection and testing device which facilitates accurate timing of exposure of various reagent strips to the specimen. In order to correctly test the specimen for the presence of various substances, various reagent strips must be exposed to the specimen and then evaluated after a precise period of time has passed. Inaccurate timing will yield inaccurate test results. The invention combines the features of keeping a specimen safely sealed from contact with medical personnel with a method for keeping specimen separate from reagent until medical personnel desire specimen testing to commence, facilitating accurate timing of the exposure of specimen to reagent and hence accurate test results.

Another object of the invention is to provide a fluid specimen collection and testing apparatus which has a temperature sensor. The temperature sensor is used to read the temperature of the fluid specimen at the time the specimen is deposited into the collection and testing apparatus. Medical personnel can refer to the temperature sensor to determine whether the specimen is genuine and fresh, or whether it may be a false specimen (such as tap water) or a substitute specimen (e.g. the specimen of another person, carried to the testing center by the patient and then placed into the collection and testing apparatus).

Another object of the invention is to provide a means for exposing reagent strips to specimen in a manner which allows accurate timing of exposure and which does not involve the use of an open container. Several embodiments of the invention include one or more reagent strips within the interior of the collection and testing apparatus, shielded from exposure to specimen until exposure is desired by medical personnel. Other embodiments allow placing an accessory embodying reagent strips on the collection and testing apparatus and exposing the reagent strips to specimen by a manual articulation of the collection and testing apparatus.

Another object of the invention is to provide a specimen collection and testing apparatus which can expose one specimen to multiple reagents simultaneously, providing simultaneous testing for numerous substances or medical conditions. The reagent strip used in the invention may include a reagent strip which has a plurality of sections of different reagents so that when the specimen is allowed to contact the reagent strip, the several reagent patches will simultaneously perform several tests on the specimen.

Another object of the invention is to provide a specimen collection and testing apparatus which can expose one specimen to multiple reagents in sequence over time. Several embodiments of the invention include an accessory fitting which is placed onto the apparatus to perform a particular test with particular reagents. Then the accessory fitting may be removed, another fitting placed onto the apparatus, and another test using different reagents performed.

Another object of the invention is to provide a transparent specimen collection and testing apparatus so that color of specimen may be observed, both for possibility of a false specimen and for the presence of visible substances or color which may indicate health problems (e.g. blood in the urine).

Another object of the invention is to provide a specimen collection and testing device which, after initial testing, may remain sealed and may be shipped to another laboratory for further testing and analysis of the specimen. For further testing, specimen may be removed from the device, such as by removing specimen from absorbent material within the device, without risk of damaging the integrity of the specimen and without giving rise to the possibility of inaccurate test results.

Another object of the invention is to provide a means for collecting hazardous fluids in a testing device without exposing the outside of the device to the fluid. In all embodiments of the invention, specimen will be collected and then sealed within the interior of the container with the specimen not having any contact with the exterior of the container during normal use.

Another object of the invention is to provide a fluid specimen collection and testing device which keeps the specimen covered at all times and need not be uncovered in the laboratory to accommodate testing.

Another object of the invention is to provide a fluid specimen collection and testing apparatus which is simple in design and construction, safe to use, and inexpensive to manufacture.

Another object of the invention is to provide a specimen collection and testing apparatus which is compact, light weight, easy to handle and simple to use.

Another object of the invention is to provide a specimen collection and testing apparatus which is simple, durable and reliable enough to use to accommodate in-home use for self-testing, use by police forces to test criminal suspects, use by highway patrol officers to test truckers at port of entry facilities or to test other motorists, and use for testing personnel working in various safety-related occupations, such as airline, railroad and shipping workers.

Another object of the invention is to provide a fluid specimen collection and testing apparatus which may be used in a veterinary setting, whether by pet owners, veterinarians, agricultural workers, zoo keepers, or others.

Another object of the invention is to provide a means for collecting, containing and testing fluids for various effluents, such as hazardous chemicals.

Other objects and advantages of the invention will become apparent from the specification, drawings and claims.

III. BRIEF DESCRIPTION OF THE DRAWINGS

FIGS. 3 and 3A depict partially exploded perspective views of another preferred embodiment of the invention with some parts shown in phantom.

FIGS. 5 and 5A depict components used in one preferred embodiment of the invention.

IV. DETAILED DESCRIPTION OF THE PREFERRED EMBODIMENT

Figure 1:
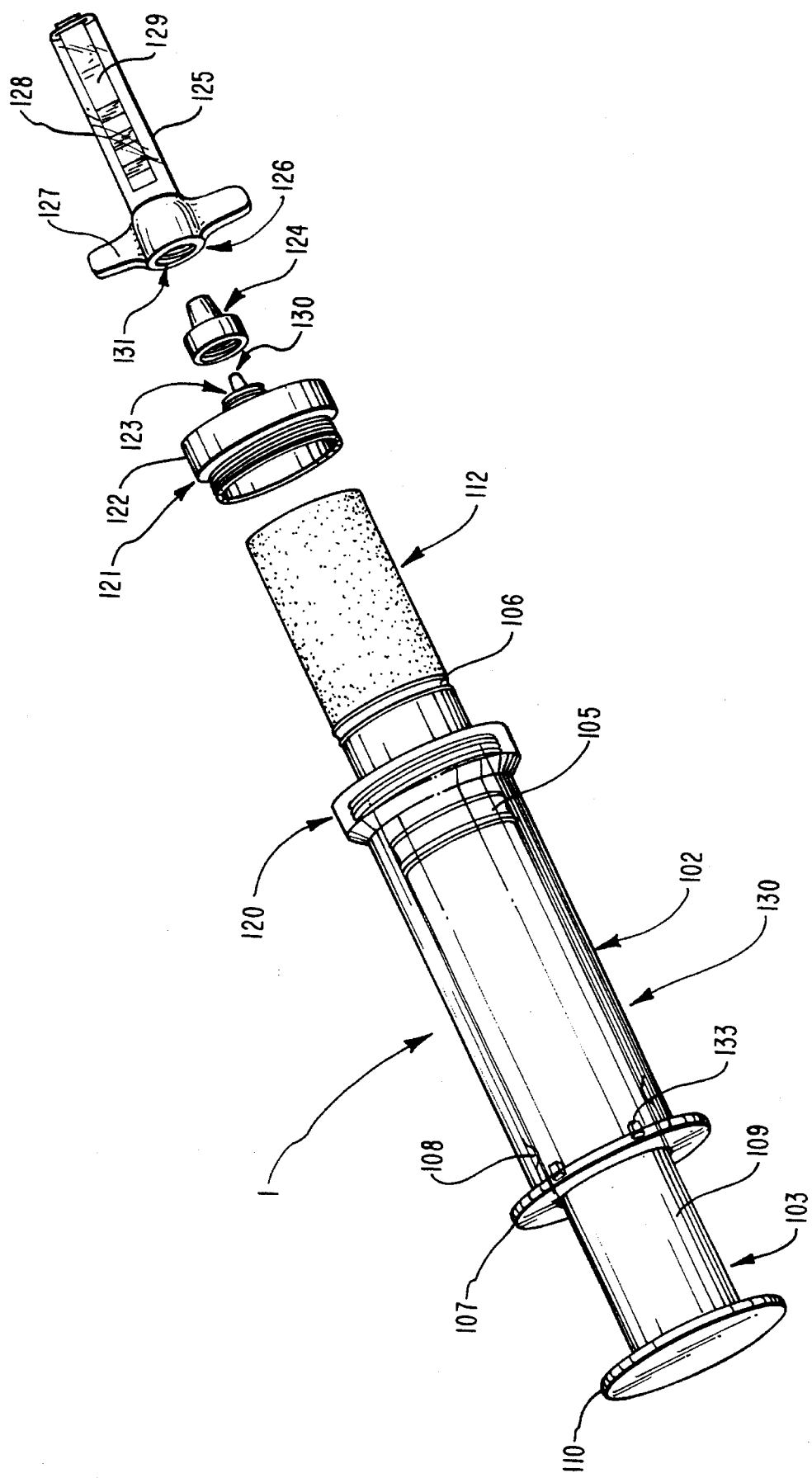
FIG. 1 depicts a partially-exploded perspective view of one preferred embodiment of the invention.

Referring to FIG. 1, one preferred embodiment of the invention is shown. The fluid collection and testing apparatus 1 has as its major components a plunger 103, barrel 102, a barrel adapter 122 and an accessory tip 125. The barrel 102 is composed of a gripping ridge 107, a body 130 and threads 120 at its distal end and a gripping ridge 107 at its proximal end. Within the body 130 is located a slidable, sealing plunger 103. The plunger 103 consists of a handle 110 at its proximal end, a shaft 109, sealing rings 105 and 106 and absorbent material 112 at its distal end. Absorbent material 112 may be affixed to the plunger 102 and/or sealing rings 105 and 106 by glue, epoxy, head bonding, by use of a structural internal rod or any other means to achieve firm engagement between the absorbent material 112 and plunger 103. The invention may also include a plunger stop 133 which prevents removal of the plunger 103 from barrel 102 once assembled to prevent tampering with specimen held in absorbent material 112. Sliding action of the plunger 103 is guided by plunger guards 108 and sealing rings 105 and 106.

Mountable to the barrel by means of the threads 120 is a barrel adapter 122 with threads 121 for fluid-tight mating with threads 120 on the barrel. The barrel adapter 122 also includes a male luer lock 123 and transmitting aperture 130 in the center of male luer lock 123 for use in expelling a quantity of fluid specimen from within the barrel 102. Luer locks are well known in the prior art, and threads or snap-rings could be used in their place. Male luer lock 123 may be sealed in fluid-tight fashion with a removable luer cap 124 which covers the transmitting aperture 130. Male luer lock 123 is adapted to accept an accessory tip 125. The accessory tip 125 includes female luer lock 126 and receiving aperture 131 for receiving a fluid specimen transmitted from the barrel 102 by way of the transmitting aperture 130. The female luer lock 126 is adapted for mating with the male luer lock 123 and includes wings 127 to facilitate gripping by the user's fingers. In the preferred embodiment, the luer locks used are of dimensions incompatible with any hypodermic needle luer lock fitting to prevent misuse of the apparatus. Standard luer locks may be used as well, however A clear sleeve 128 attached to the female luer lock 126 in fluid-tight engagement, the sleeve 128 having a reagent strip 129 located within it. Sleeve 128 is attached to the accessory tip 125 by glue, epoxy, heat bonding, welding, or any other suitable method. In alternative embodiments, the accessory tip 125 may be mountable directly with said barrel 102. The plunger 103, barrel 102, barrel adapter 122, male luer look 123 and female luer lock 126 could be made from plastic, stainless steel, glass or other materials. In the preferred embodiment they are made from plastic. Sealing rings 105 and 106 are made from rubber and sleeve 128 is made from flexible clear film, although other materials, such as plastic, could be used instead.

In use by a patient, the barrel adapter 122 is removed from the barrel 102, and the plunger 103 is articulated so that the absorbent material 112 protrudes from the distal end of the barrel 102 beyond the threads 120. The patient then causes the absorbent material 112 to come into contact with a specimen, such as by placing it in the path of a stream of urine exiting the human body, or by dipping it into the fluid to be tested. The absorbent material 112 absorbs a quantity of the specimen for testing. Hydrophilic foam is used as the absorbent material 112 in the preferred embodiment so that fluid specimen is quickly and easily absorbed and retained.

The patient then retracts the plunger 103 within the barrel 102 causing the absorbent material 112 to be located entirely within the barrel body 130 between the proximal and distal ends of the barrel 102. The patient then seals the fluid collection and testing apparatus 1 by installing the barrel adapter 122 with sealing luer cap 124 in place. At this point a fluid specimen has been collected and safely sealed in fluid-tight confinement within the fluid collection and testing apparatus 1.

A person responsible for testing the specimen, such as a nurse, then takes the fluid collection and testing apparatus 1, removes the luer cap 124 and attaches accessory tip 125 by means of the luer lock. The nurse then slides the plunger 103 within the barrel body 130 toward the distal end of the barrel 102 and the barrel adapter 122, causing the absorbent material 112 to be pressed against the barrel adapter 122, forcing a portion of the fluid specimen from the absorbent material 112, through the transmitting aperture of the male luer lock 123 and the receiving aperture of the female luer lock 126 and into the sleeve 128 where it contacts reagent strip 129. The nurse times exposure of specimen with reagent and notes and records any color change in reagent strip 129. At this point, testing of the specimen is complete. The fluid collection and testing apparatus 1 may then be discarded with specimen safely contained within its interior, or the accessory tip 125 may be removed and another accessory tip 125 may be installed and a second test performed on the specimen. This procedure may be repeated numerous times due to the large quantity of specimen which the absorbent material 112 is capable of holding and the small quantity of specimen required for exposure to reagent strip 129. Alternatively, the luer cap 124 may be placed onto the barrel adapter and the device with fluid sealed within its interior sent to another laboratory for further testing. If necessary, specimen could be removed from the device entirely by removing luer cap 124 and forcing a quantity of fluid specimen from the absorbent material 112 through the transmitting aperture 130 and into a secondary container such as a test tube.

The plunger handle 110, gripping ridge 107, barrel body 130, and wings 127 aid the user in gripping and manipulating the fluid collection and testing apparatus 1. The sealing rings 105 and 106 form fluid-tight seals within the barrel body 130 to prevent any escape of specimen beyond the barrel base. Fluid-tight seals are also formed by the barrel adapter 122 with barrel 102, by luer cap 124 with male luer lock 123, and by female luer lock 126 with male luer lock 123. Plunger guides 108 maintain plunger 103 alignment within the barrel body 130. Threads 120 and threads 121 form a fluid-tight seal between barrel 102 and barrel adapter 122 to prevent any escape of specimen. Luer cap 124 forms a fluid-tight seal with male luer lock 123. Similarly, female luer lock 126 of accessory tip 125 forms a fluid-tight seal with male luer lock 123.

The absorbent material 112 is a means for collecting a fluid specimen or a means for absorbing a fluid specimen. The combination of sealing rings 105 and 106, barrel adapter 122 and luer cap 124 or accessory tip 125 serve as a means for containing a fluid specimen in fluid-tight confinement, a means for sealing a fluid specimen within a container or within an enclosure, and a means for isolating a fluid specimen from contact with personnel transporting, handling or testing the specimen. Reagent strips 129 in conjunction with absorbent material 112, barrel adapter 122 and accessory tip 125 comprise a means for testing a fluid specimen. Plunger 103, absorbent material 112, barrel adapter 122, transmitting aperture 130, receiving aperture 131 and clear sleeve 128 combine to serve as a means for communicating a fluid specimen from absorbing means to testing means.

In the preferred embodiment of the invention, the barrel 102 is manufactured from clear plastic such as that found in prior art syringes. Plunger 103 is also manufactured of plastic as found in prior art syringes and sealing rings 105 and 106 are made from rubber and are typical of those found in the prior art. Absorbent material 112 may be any material which can absorb a fluid specimen, such as cloth, foam or other material. In the preferred embodiment, hydrophilic foam is used as absorbent material 112. In the preferred embodiment, sleeve 128 is made of flexible, clear film, although any other fluid-tight material which allows observation of reagent strips 129 may be employed. White absorbent material 112 is used in the preferred embodiment to permit testing personnel to readily ascertain the color of the fluid specimen being tested. Barrel 102 is clear in the preferred embodiment to permit such color observation. Similarly, sleeve 128 must be transparent and preferably clear and colorless to permit color observation by testing personnel.

In alternative preferred embodiments, threads 121 and 122 could be omitted and a snap fitting or any other fluid-tight connection, including a one-way snap ring could be used. Use of a non-resealable one-way snap ring in place of threads 121 and 122 would prevent tampering with the specimen after the barrel adapter has been installed onto the barrel 102. Alternatively, luer cap 124 could be mounted with a one-way or non-resealable manner to prevent tampering. Male luer lock 123 and female luer lock 126 could be replaced with any means for removably attaching an accessory tip 112 so that reagent strip 129 may be placed in fluid communication with the absorbent material 112.

Fluid communication with the absorbent material 112 is achieved when specimen is forced from the absorbent material, through male luer look 123, and through female luer lock 126 into the sleeve 128 where it contacts reagent strip 129. Multiple reagent dots of various types may be present on the strip 129 within the sleeve 128 for simultaneously testing the specimen for multiple substances or conditions. Reagent strips 129 may be replaced or accompanied by any other means for testing a fluid specimen, such as by means of a mass spectrometer or other electronic sensing device. The combination of absorbent material 112 within barrel 102, barrel adapter 122 mounted on barrel 102, male luer lock 123 including aperture on barrel adapter 122, female luer lock 126 including aperture on accessory tip 125 mountable to male luer lock 123, and reagent strips 129 within accessory tip 125 comprise a means for causing specimen to be in fluid communication with reagent strips 129.

Figure 2:
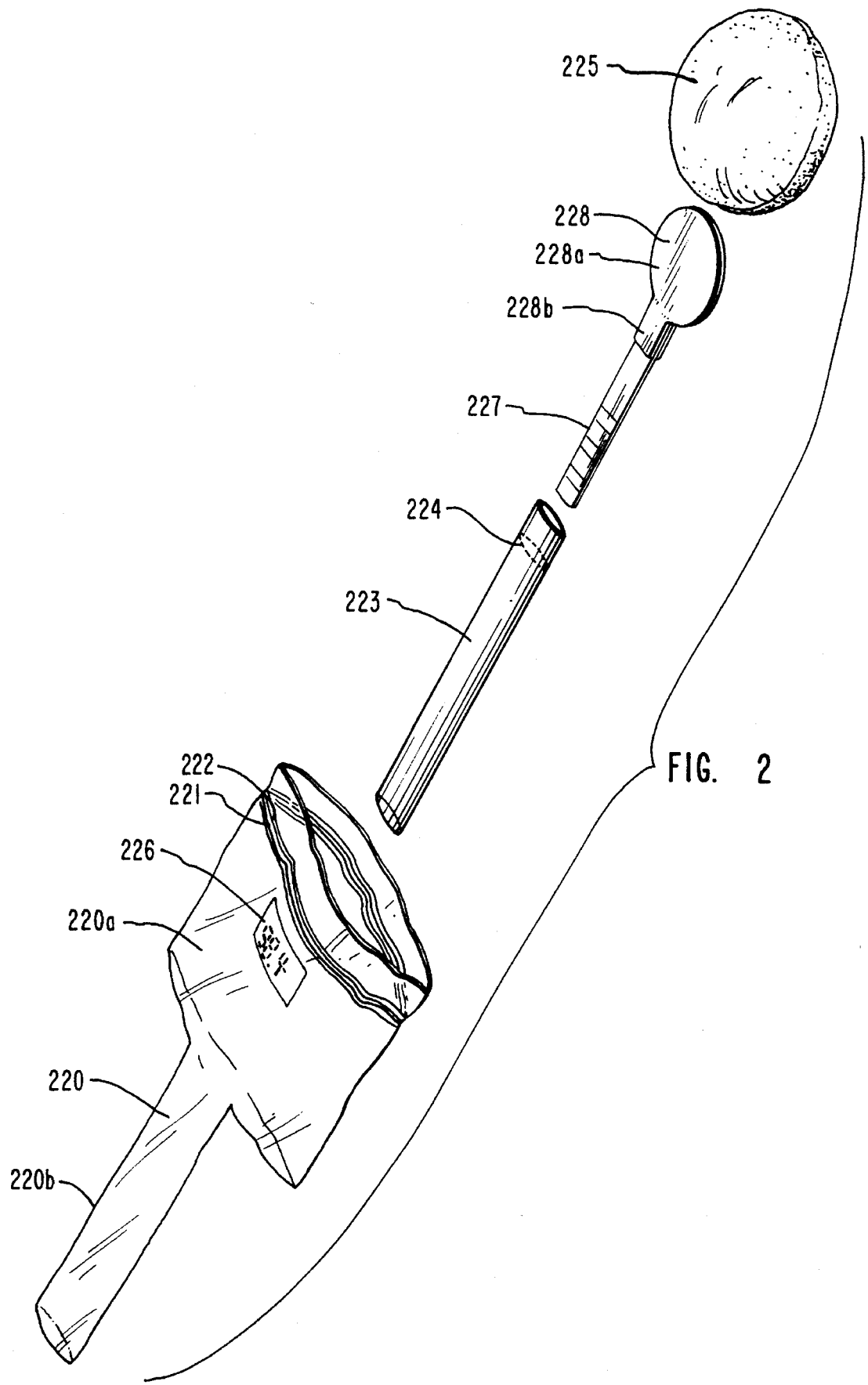
FIG. 2 depicts a perspective view of another preferred embodiment of the invention with some parts shown in phantom.

FIG. 2 depicts an alternative preferred embodiment of the fluid specimen collection and testing apparatus 1. It includes a semi-rigid hollow straw 223 with longitudinal axis, a proximal end at one end of the longitudinal axis and a distal end at the other end of the longitudinal axis, the straw 223 having scoring 224 on all sides of the straw near its distal end and having a rigid sponge sub-frame 228 mounted at the distal end of the straw 223 beyond scoring 224. The hollow straw 223 may be of any shape that includes proper fluid isolation and fluid communication abilities described herein, such as round, square, or other shape in cross section. In the preferred embodiment the straw 223 is white opaque plastic to hide presence of the reagent strips from the patient, although other materials, including clear plastic, may be used for the straw as well. The rigid sponge sub-frame 228 comprises a circular portion 228a and a rectangular portion 228b and is plastic in the preferred embodiment. The rectangular portion 228b is mountable within the straw 223 at the straw's distal end adjacent the scoring 224 and the circular portion 228a extends beyond the end of the straw. Mounted about the exterior of the rigid sponge sub-frame 228 is hydrophilic sponge material 225 which has the ability to absorb and retain a fluid specimen. Mounting may be accomplished by fluid, epoxy, heat bonding or otherwise. Mounted within the straw 223 between the scoring 224 and in fluid isolation from the hydrophilic sponge 225 is a reagent strip 227. The reagent strip 227 must be in fluid isolation from the exterior of the straw to prevent premature contact of reagent strip 227 and specimen. The reagent strip 227 is maintained within the straw 223 in fluid isolation from specimen until the straw 223 is broken at the point of scoring or at any other point. Fluid isolation of reagent strip 227 within straw 223 may be accomplished with any type of known closure or fluid-tight seal on straw 223 ends to prevent contact of specimen and reagent strip 227 until such contact is desired. Specimen may be exposed to multiple reagents simultaneously by using reagent strips containing multiple reagents. At the time of assembly, the entire straw 223 and sponge 225 assembly is located within a sealable fluid-tight plastic film enclosure 220. In the preferred embodiment, enclosure 220 is constructed from clear polymer film, although many other rigid or flexible fluid-impermeable materials could be used equally successfully. The enclosure 220 consists of a head portion 220a and a tail portion 220b. The head portion 220a includes one or more seals 221 and 222, such as those found on resealable plastic bags, adhesive seals, or other seals. The head portion 220a also includes a temperature strip 226. The shape of enclosure 220 is not critical and other shapes would serve as well.

In use, the user removes the straw 223 and sponge 225 assembly far enough from the enclosure 220 to expose the sponge 225 to a fluid specimen, such as a stream of urine or by dipping the sponge 225 into any container of fluid specimen. Removal of the sponge 225 and straw 223 from enclosure 220 may be accomplished by simply folding enclosure 220 away from the sponge 225. When the sponge 225 is exposed to a specimen, the sponge 225 absorbs and retains or holds a quantity of specimen. The user then holds the straw 223 tilted downward and slides the enclosure 220 downward over the sponge 225. The use of absorbent material for the sponge 225, such as hydrophilic foam, prevents any dripping of specimen during this process. Alternatively, closure of the apparatus may be achieved by the user holding the enclosure 220 in an upright position, allowing gravity to pull the straw 223 and sponge 225 assembly fully into the enclosure 220. The user then closes the seals 221 and 222. At that point, the temperature strip 226 will indicate the temperature of the specimen, permitting medical personnel to observe the temperature of the specimen to determine whether it is a genuine or false specimen. The seals 221 and 222 may be non-resealable to prevent any tampering with the specimen after it has been placed into the enclosure 220. When used as described, a specimen is held in sealed fluid-tight confinement within the enclosure 220 and in fluid-isolation from the reagent strip 227.

Medical personnel, such as a nurse, then grasps the tail portion 220b of the enclosure 220 and grips the rigid or semi-rigid straw 223 with one hand. The other hand is used to apply pressure to the rigid sponge sub-frame 228 and cause it to deviate from the longitudinal axis of the straw 223 and making the reagent strip 223 visible to the nurse. This deviation causes a break or fluid-permeable opening in the straw at the scoring 224, permitting fluid communication from the sponge 225 to the reagent strip 227 through the hollow center of the straw 223. Specimen may be forced from the absorbent material 225 to the reagent strip 227 simply by squeezing absorbent material 225 with the fingers. Reagent strip 207 is in fluid isolation from the sponge 225 until a break in the straw 223 at the scoring 224 is achieved, when specimen contacts the reagent strip 227. The nurse then times the exposure of the reagent strip 227 to specimen, notes color changes and records test results. The fluid specimen collection and testing apparatus 1 is then discarded with the fluid specimen sealed within its interior. Alternatively, the entire fluid specimen collection and testing apparatus could be transported to another laboratory for removal of specimen and further testing. During the entire testing process and during disposal, the specimen was isolated from medical personnel by the enclosure 220 and the risk of contact between medical personnel and specimen was minimal.

Hydrophilic sponge 225 serves as a means for collecting and retaining a fluid specimen. Enclosure 220 and seals 221 and 222 serve as a means for enclosing or containing a fluid specimen in fluid-tight confinement within an enclosure or container. Sponge 225, hollow straw 223, and reagent strip 227 comprise a means for testing a fluid specimen. Reagent strip 227 by itself is also considered a means for testing a fluid specimen. Sponge 225, hollow straw 223 and scoring 224 comprise a means for communicating a fluid specimen to a means for testing a fluid specimen.

FIG. 3 depicts an alternative embodiment of the invention. It includes a barrel 602 which has holes 631 at its proximal end to accommodate one or more rods 609(a) and 609(b) in fluid-tight engagement with the holes 631, the rods 609(a) and 609(b) being part of the shaft 609 of a plunger 603, the plunger also having a plunger handle 610 at its proximal end. Within the barrel 602 and moveable through the interior of the barrel 602 by sliding articulation of the plunger rods 609(a) and 609(b) through the holes 631 is a cone-shaped plunger head 632 mounted to the distal end of the plunger 603, the plunger head 632 having a hole 640 at its center. The plunger head 632 and plunger 603 are permanently mounted to each other to prevent removal of plunger 603 from barrel 602 and tampering with specimen. Holes 631 and plunger rods 609(a) and 609(b) are constructed to such tolerances and with such materials that a fluid-tight seal is created to prevent the escape of any specimen from barrel 602. This may be accomplished by using rubber rings on the interior surface of holes 631. The plunger head 632 is in fluid-tight engagement with the inside surface of barrel 602. An air escape tube 650 is located within the barrel 602. A notch 651 in the plunger head 632 accommodates the air escape tube during sliding motion of the plunger 603, permitting air to escape from the barrel 602 during use.

Insertable into the proximal end of the barrel 602 is a portion of absorbent material 612, such as hydrophilic foam or other means for absorbing a fluid specimen, the absorbent material 612 being mounted onto a rigid or semi-rigid rod 612(a), such as a plastic rod, which is in turn mounted to the proximal end of a transparent testing chamber 634 adjacent a plurality of holes, perforations or fenestration 634. The chamber 635 includes one or more sealing rings 605 about its exterior diameter for fluid-tight sealing engagement with channels 633 located within barrel 602. The chamber 634 also includes a fluid-tight resealable insertion hole 630, such a heimlich valve or other fluid-tight orifice, into which a reagent strip 629 may be inserted for testing fluid specimen located in the chamber 634. An optional sealing cap 622 mountable to the chamber 634 in fluid-tight engagement therewith is included. In the preferred embodiment, absorbent material 612 is white and barrel 602 and chamber 634 are clear or have clear viewing windows to accommodate observing the color of specimen and reagent strip 627. In the preferred embodiment, the barrel 602, plunger 603 and chamber 634 are constructed of plastic although other materials could be used. Also in the preferred embodiment, plunger head 632 and sealing ring 605 are rubber.

In use, the barrel 602 portion of the invention and chamber 634 portion of the invention are initially separate. The absorbent material 612 is first exposed to fluid specimen which it absorbs and retains. Then the absorbent material 612 is moved into the interior of barrel 602 through its distal end until sealing ring 605 engages and forms a fluid-tight seal with channel 633. Alternatively, barrel portion 602 and chamber portion 634 could be fitted with matching fluid-tight threads so that they could both be joined and a seal formed by use of the threads. Any other suitable means for joining two devices with interior voids in fluid-tight engagement could be used as well. A one-way snap-ring or ratchet lock could be used for fitting chamber 634 with barrel 602, preventing removal thereafter and hence aiding in the prevention of specimen tampering. When chamber 634 and barrel 602 are joined, a fluid specimen has been collected and safely sealed within a fluid-tight container. The fluid specimen may then be safely transported within the sealed confines of the invention, or it may be tested immediately. If transport is desired, typically a sealing cap 622 would be placed onto the chamber 634 providing a backup or safety seal in addition to the sealing insertion hole 630 by forming another fluid-tight seal around the distal end of the chamber.

For testing the specimen, the plunger 603 may be moved into the barrel 603, causing plunger rods 609(*a*) and 609(*b*) to push plunger head 632 against absorbent material 612 and compress against the proximal end of the chamber 634, forcing a quantity of fluid specimen from absorbent material 612, through holes 635 and into the testing chamber 634. During this movement, rod 612(*a*) will pass through cone central hole 640 keeping the absorbent material 612 aligned while allowing its needed compression. Air would be displaced within the device during this process by the cone 632 and would be accomodated by the air escape tube 650 mounted in barrel 602 to prevent any air compression within the barrel 602. The specimen may not exit the testing chamber 634 to the outside because the insertion hole 630 maintains a fluid-tight seal. Then one or more reagent strips 629 may be inserted into the testing chamber 634 through the insertion hole 630, causing the reagent strip 629 to come into contact with the fluid specimen. Exposure of the reagent strip 629 to the fluid specimen is timed and color change in the reagent strip noted. Additional reagent strips may also be inserted into the chamber 634 through insertion hole 630 to perform multiple tests. Alternatively, reagent strips 629 may be inserted into the chamber 634 prior to introduction of a quantity of specimen into the chamber 634. When testing is complete, the entire invention with specimen still sealed within its interior may be safely shipped or transported to another laboratory for further testing.

The absorbent material 612 is considered a means for collecting and retaining a fluid specimen. The combination absorbent material 612 within barrel 602, sealing ring 605 and channel 633, fluid-tight insertion hole 630 and optional sealing cap 622 comprise a means for containing a fluid specimen in fluid-tight confinement, a means for sealing a fluid specimen within a container or enclosure, and a means for isolating a fluid specimen from contact with personnel handling, transporting or testing the specimen. The combination of plunger 603, cone 632, absorbent material 612, holes 635, testing chamber 634, insertion hole 630 and reagent strips 629 serve as a means for testing a fluid specimen. The reagent strip 629 alone is also a means for testing a fluid specimen.

Figure 4:
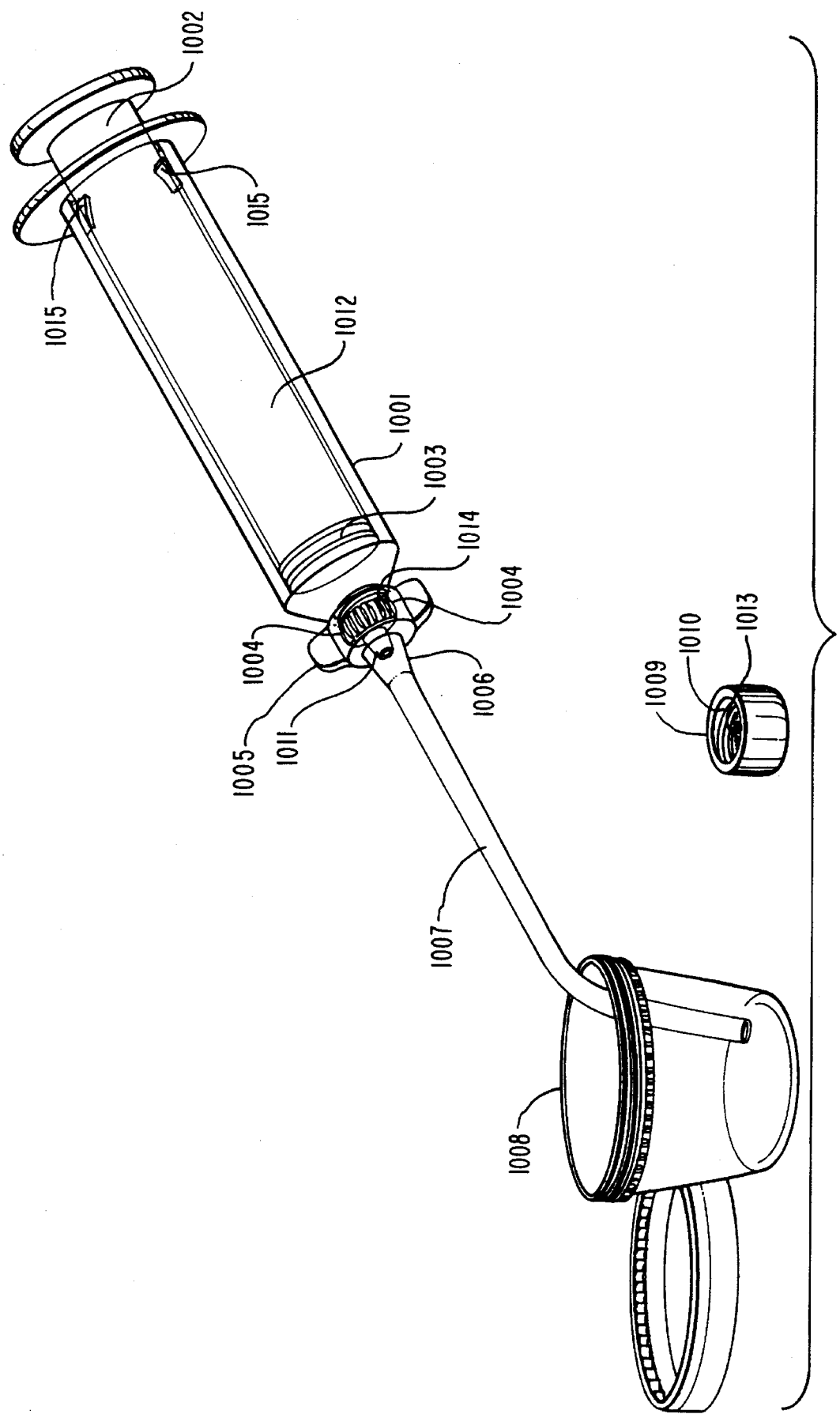
FIG. 4 depicts another preferred embodiment of the invention.

FIG. 4 depicts another embodiment of a fluid specimen collection and testing device. It includes a syringe 1001 with a barrel 1012, plunger 1002, sealing rubber plunger end 1003 for creating a fluid-tight seal within the barrel 1012, and syringe tip 1011 including male luer lock 1004 and locking ratchet teeth 1013. The syringe 1001 could be of a type typical of prior art syringes, but in the preferred embodiment, the luer lock utilized is one incompatible hypodermic needle luer locks or other unrelated medical apparatus so that misuse of the device is prevented. Also in the preferred embodiment, other distinguishing characteristics are added to the syringe 1001, such as a slightly different shape than prior art syringes or a colorful stripe down the side of the barrel 1012 to aid medical personnel in distinguishing it from syringes used for administering injections.

Attachable and detachable to the syringe tip 1011 and male luer lock 1004 is an accessory tip 1005 including a female luer lock 1006 and a fluid collection tube 1007 mounted in fluid-tight engagement with the accessory tip 1005. Also used in conjunction with the invention is a fluid vessel or cup 1008. Mountable to syringe tip 1011 at the luer lock is luer cap 1009 which includes an interior cavity 1010 with locking ratchet teeth 1013 in the cavity 1010. When cap 1009 is screwed onto syringe tip 1011, ratchet teeth 1014 of syringe tip 1011 engage and lock with ratchet teeth 1013 of luer cap 1009. The ratchet teeth 1013 and 1014 are constructed so that luer cap 1009 can be easily screwed onto syringe tip 1011, but cannot be removed without breaking ratchet teeth 1013 or 1014. Syringe strips 1015 are located within barrel 1012 to prevent removal of plunger 1002 from barrel 1015 once assembled therein at the time of manufacture. Thus, when luer cap 1009 is placed onto syringe cap 1011, the contents of the syringe 1001 may not be accessed or tampered with without either breaking ratchet teeth 1013 or 1014 or syringe strips 1015 and providing readily ascertainable visible evidence of tampering.

In the preferred embodiment, the tube 1007 is manufactured of flexible plastic film which has a passageway through its length through which a fluid may travel. The tube 1007 is also constructed so that it will lie flat against itself in a fluid-tight fashion when not in use. Essentially, the tube 1007 is acting as a heimlich valve know in the prior art. This tube design allows the tube 1007 to be used for collecting a fluid specimen by withdrawing the plunger 1002 within syringe barrel 1012 and creating a suction force that draws a fluid specimen from the cup 1008 through the tube 1007 and syringe tip 1011 and into syringe barrel 1012. The tube 1007 may be bonded to the cup 1008 as well. This embodiment of the invention allows collection of a fluid specimen without the use of any absorbent material and the inherent filtering associated therewith. Use of a clear syringe barrel permits medical personnel to easily view the cloudiness of the specimen and observe any particulates in it. Testing of the fluid specimen could be performed by installing an accessory tip 125 as depicted in FIG. 1, or testing could be performed by expelling a quantity of fluid specimen from the syringe 1001 into any prior art testing device.

FIG. 5 depicts another embodiment of the fluid specimen collection and testing apparatus. It includes a container 1100 and a lid 1107 attachable in fluid-tight engagement with the container 1100. The container 1100 is used for collection of a fluid specimen such as by holding it under a stream of urine so that the urine may enter the container opening 1113. The container 1100 includes a temperature strip 1101 for measuring the temperature of fluid specimen to detect a false specimen. The container has a bottom 1112 and a top 1112. Near the top 1113 are located threads 1102 for engagement with the threads 1106 (shown in phantom) of the lid 1107 in a fluid-tight manner, such as by sealing at the edge 1105 and container lip 1103 against container and cap respectively.

The cap includes a resealable fluid-tight valve or opening for receiving reagent strips into a testing passage 1109. The testing passage is comprised of a hollow tube constructed of plastic film or another device utilizing two film layers 1111a and 1111b lying in substantially flat contact with each other. Each layer has a first edge and a second edge along its length and a first end and a second end along its width (not numbered). The lower of the two film layers 1111b has an aperture 1110 in it. The first edge of the first film layer is joined in fluid-tight connection to the first edge of the second film layer, the second edge of the first film layer is joined in fluid-tight connection to the second edge of the second film layer, the second end of the first film layer is joined in fluid-tight connection to the second end of the second film layer, and the first end of the first film layer and the first end of the second film layer are joined about the periphery of the opening 1108. This combination forms a substantially flat tube with a longitudinal passage therein, the longitudinal passage being connected to the opening 1108 and the tube having an aperture 1110 on one side of its length. An object may be inserted through opening 1108 into the tube and exposed through aperture 1110 to the contents of container 1100. This design permits objects, such as reagent strips, to be inserted into testing passage 1109 while maintaining a fluid-tight seal and preventing any escape of fluid specimen from the container. FIG. 5a depicts the tube in greater detail.

In use, once a fluid specimen is collected in the container 1100, the lid 1107 is sealed to the container 1100. At that point a fluid specimen is sealed in fluid-tight with the device. Then a reagent strip is inserted through the aperture 11108 causing it to be between the two film layers 1111a and 1111b with a portion of the reagent strip exposed through aperture 1110. Inversion of the container 1100 causes fluid specimen to contact the reagent strip. Timing of exposure and recordation of test results can then be performed.

This embodiment of the invention permits viewing the specimen in container 1100 for color, cloudiness, and particulates. It also permits safe shipping of a fluid specimen sealed within the device. Further testing of the fluid specimen may ba accomplished by removing the lid 1107 and removing fluid specimen for testing in other containers.

Figure 6:
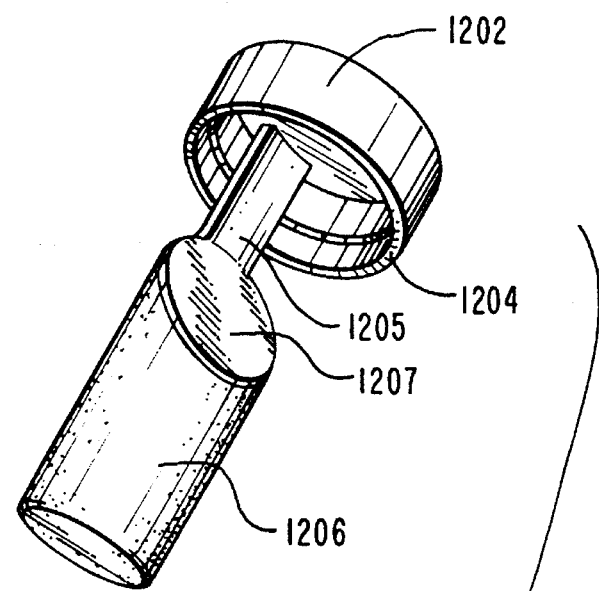
FIG. 6 depicts another preferred embodiment of the invention.
Figure 6:
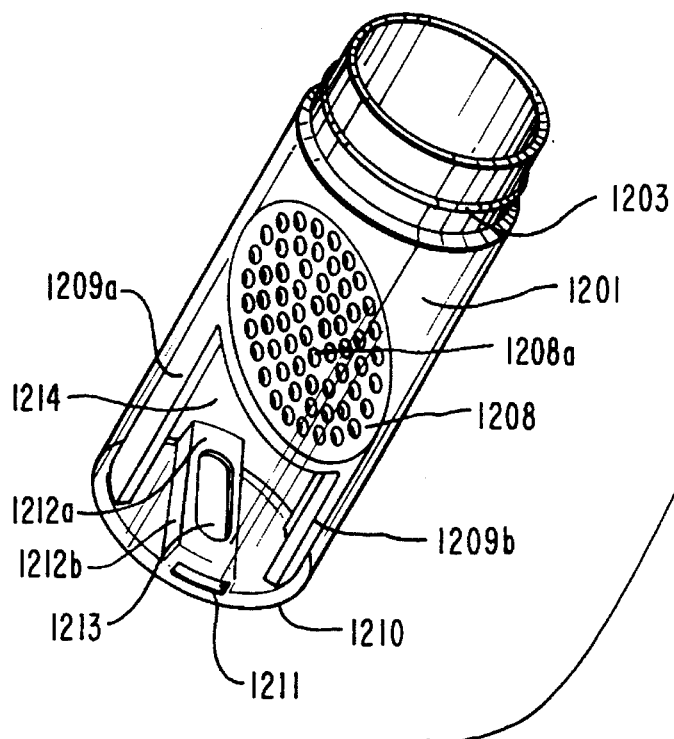

FIG. 6 depicts an alternative embodiment of the invention. It includes a container 1201 and lid 1202. The container includes a sealing snap-ring 1203 for sealing with a snap-lip 1204 on the lid 1202 in fluid-tight engagement therewith. The lid 1202 includes a post 1205 mounted to its interior onto which an angled platform 1207 is mounted. The post 1205 and angled platform 1207 comprise a means for supporting absorbent material 1206. Absorbent material 1206 or other means for absorbing and retaining a fluid specimen is affixed to the platform 1207. The container includes an angled sieve 1208 with sieve holes 1208a, the sieve 1208 being angled in a manner roughly similar to the platform 1207. The sieve 1208 is mounted on support posts 1209a and 1209b. At the bottom 1210 of the container 1201 an opening 1211 including a resealable fluid-tight valve is found into which reagent strips or other objects may be inserted. The opening 1211 leads to a testing passage comprised of a hollow tube constructed of plastic film or another device utilizing two film layers 1212a and 1212b lying in flat contact with each other. The upper of the two film layers 1212a has an aperture 1213 in it. When a reagent strip is inserted through opening 1211 it contacts specimen in the container 1201 through the aperture. This design permits objects to be inserted into opening 1211 while maintaining a fluid-tight seal and preventing any escape of fluid specimen from the container.

In use, the absorbent material 1206 would be exposed to a fluid specimen and permitted to absorb a quantity of it. The lid 1202 would then be placed onto the container 1201 until the snap-ring 1203 and snap lip 1204 engage in a fluid-tight manner. The action of placing the lid 1202 onto the container 1201 to cause a closure of snap-ring 1203 and snap-lip 1204 pressed absorbent material 1206 against sieve 1208 and forces fluid specimen from the absorbent material into the container testing area 1214 where it may contact a reagent strip through the aperture 1213.

Figure 7:
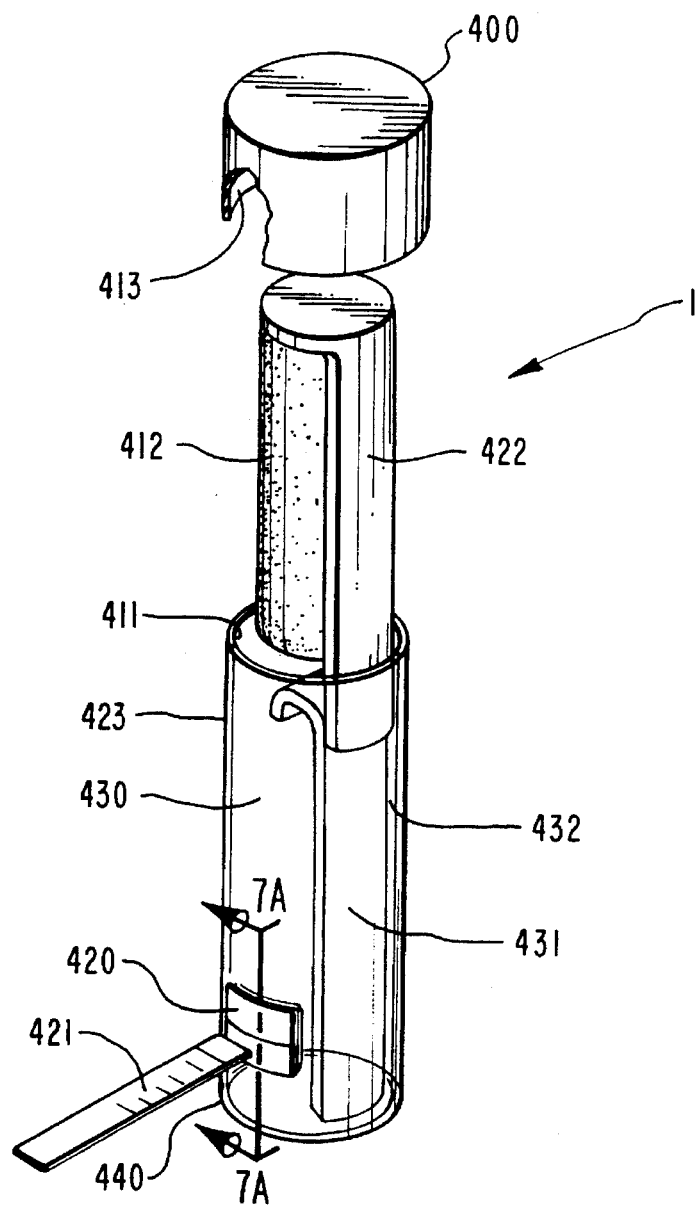
FIGS. 7 and 7A depict cut-away views of another preferred embodiment of the invention.

Referring to FIG. 7, one preferred embodiment of the invention is shown. It includes a hollow body or container 423 having a longitudinal axis, an open end, a closed end, a container wall (not numbered) and a testing area 430 within its interior. The container 423 has a fluid-tight opening 420 near its proximal end into which reagent strips 421 may be inserted to test specimen within the testing area 430. The opening 420 could be a heimlich valve or other fluid-tight resealable valve through which reagent strips or reagent rods may be inserted for contact with a fluid specimen. More detail concerning possible valves for use in opening 420 is given in the description accompanying FIGS. 7a, 5 and 5a.

Within the body 423 is affixed a rigid squeezing rod 431. Protruding from the body 423 is a section of absorbent material 412 mounted onto a rigid sub-frame 422. The body 423 also includes a fluid sealing lip 411 for making a fluid-tight seal with the cap sealing lip 413 of cap 400. A drain plug 440 is included on the body 423 for use in draining a quantity of fluid specimen from the body 423 into another container such as a test tube for further testing of the specimen. The drain plug 440 could be a piece of tape or a rubber stopper or other fluid-tight seal over a hole or aperture in the body 423.

Figure 7A:
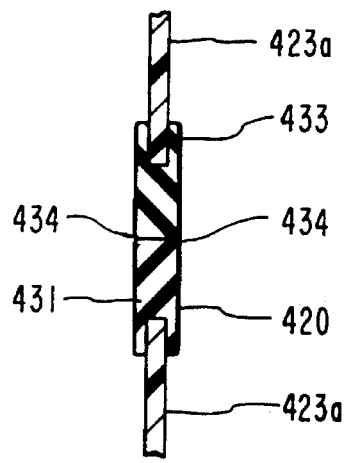

FIG. 7a depicts greater detail of opening 420. It includes the walls 423a and 423b of the body 423 in which a hole 433 is formed and into which a resealable rubber seal 431 may be inserted. The seal 431 includes an openable and resealable slit 434 through which reagent strips 421 may pass and which rebounds thereafter to keep opening 420 fluid-tight.

In use, the user exposes absorbent material 412 to a fluid specimen and then places cap 400 over absorbent material 412 until the cap lip 413 seals with the body lip 411. The action of placing cap 400 over absorbent material 412 and moving cap 412 toward the distal end of the body 423 pushes absorbent material 412 and sub-frame 422 into the hollow body 423, and rod 431 guides the sub-frame 422 and absorbent material into a retention chamber 432, compressing absorbent material 412 in the process and causing a quantity of fluid specimen to exit the absorbent material 412 and flow to the testing area 430 of body 423.

At that point the specimen is sealed within the fluid specimen collection and testing apparatus 1 and may be tested immediately or shipped to a laboratory for testing. Medical personnel can observe the presence of specimen and color of specimen through the clear body 423 in adjacent the testing area 430. Medical personnel test the specimen by inserting a reagent strip or rod 421 through fluid-tight opening 420 causing the reagent strip 421 to come into contact with the fluid specimen. Medical personnel may then remove the reagent strip 421 from the opening 420 and time exposure of the reagent strip 421 to specimen and record test results. Alternatively, medical personnel could insert reagent strip 421 through opening 420 completely into testing area 430, and observe it within testing area 430. This procedure may be repeated numerous times with various reagents to perform various tests on the specimen. When testing is completed, the fluid specimen collection and testing apparatus 1 with specimen may be discarded.

Absorbent material 412 serves as means for collection of a fluid specimen. Cap 400 and body 423 serve as means for sealing a fluid specimen in fluid-tight confinement within a container and a means for isolating a specimen from personnel handling, transporting or testing the specimen. Reagent strips 421 and fluid-tight opening 420 serve as means for testing a fluid specimen.

In the preferred embodiment, sub-frame 422 and rod 431 are made from rigid plastic although other material such as wood, waterproof cardboard or others could be used as well. Cap 400 and body 423 are made from transparent plastic in the preferred embodiment, although steel, glass or other materials could be used as well. The lips 411 and 413 seal in a manner known in the prior art, such as by use of a rubber o-ring or otherwise. Absorbent material 412 is hydrophilic foam in the preferred embodiment, although other materials such as cotton or other fibers could be used as well.

Figure 8:
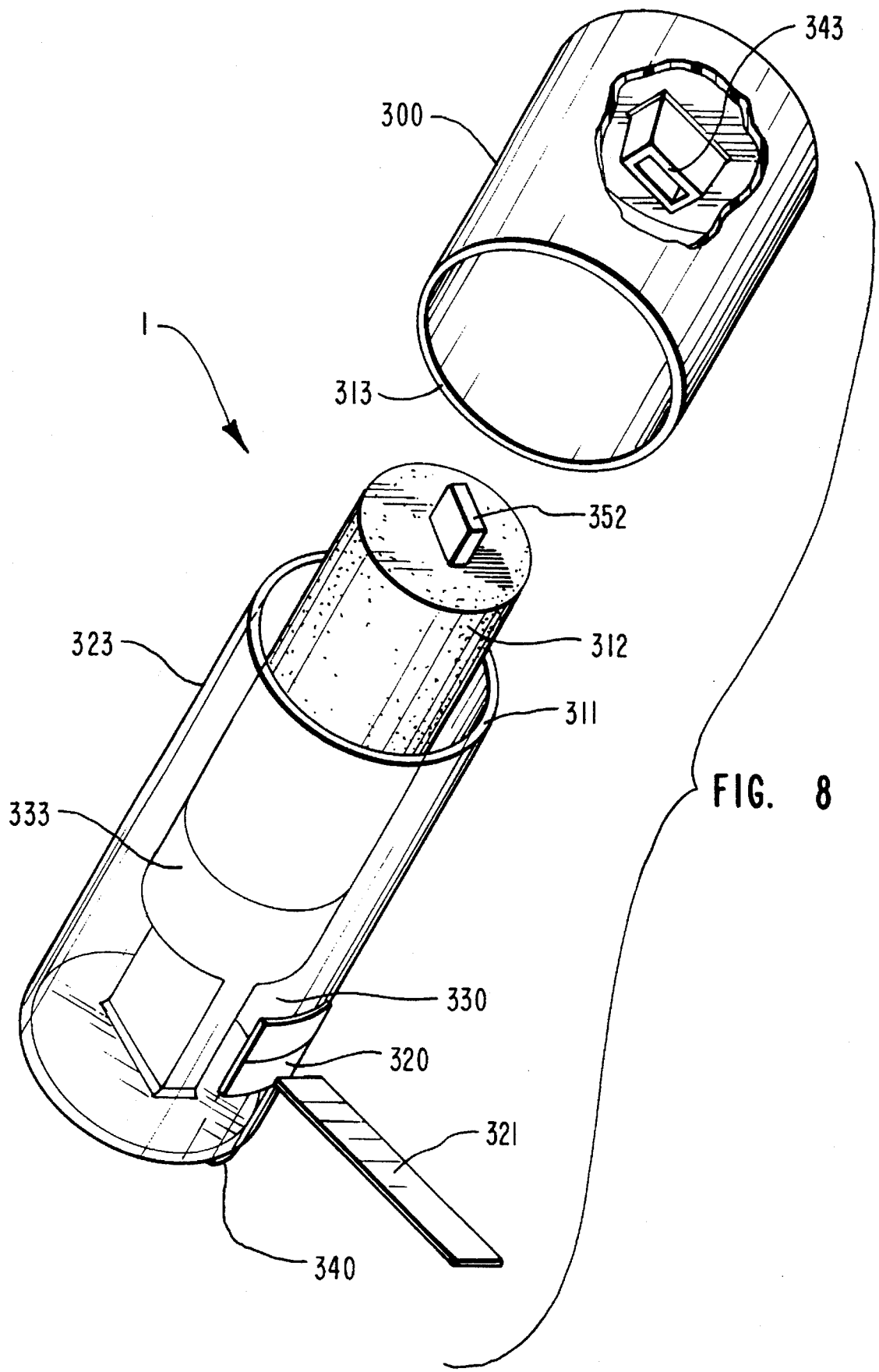
FIG. 8 depicts a cut-away view of another preferred embodiment of the invention

FIG. 8 depicts an alternative preferred embodiment of the invention. It includes a hollow body 323, cap 300, sealing lips 311 and 313, testing area 330, fluid-tight resealable opening 320 and absorbent material 312 similar to the embodiment described in FIG. 1. The body 323 has a longitudinal axis, an open end, a closed end, and a container wall (not numbered). Also shown are a post 352 mounted in absorbent material 312 for engagement with a receptacle 343 in the interior of the cap 300. The absorbent material 312 is firmly mounted to a base 333 which is in turn affixed to the body 323.

In use, absorbent material 312 is exposed to a fluid specimen which it absorbs and retains. Then cap 300 is placed onto the distal end of the body 323 so that post 352 engages receptacle 343 and sealing lips 311 and 313 mate to form a seal. At that point, the specimen is held in fluid-tight confinement within the body 323. To effect specimen testing, cap 300 and body 323 are rotated in opposite directions, resulting in a twisting or wringing of absorbent material 312 because as cap 300 is turned opposite the body 323, receptacle 343 causes rod 312 to turn the distal end of absorbent material 312 while base 333 holds the proximal end of absorbent material 312 in place. This is referred to as a means for removing a quantity of fluid specimen from absorbent material 312. As a result, a quantity of fluid specimen exits the absorbent material 312 and may flow to testing area 330, and a reagent strip 321 may then be inserted into the opening 320 for specimen testing. The combination of cap 300, receptacle 343, post 322, base 333 and body 323 are referred to as a means for twisting or wringing absorbent material 312.

Figures 9, 9A:
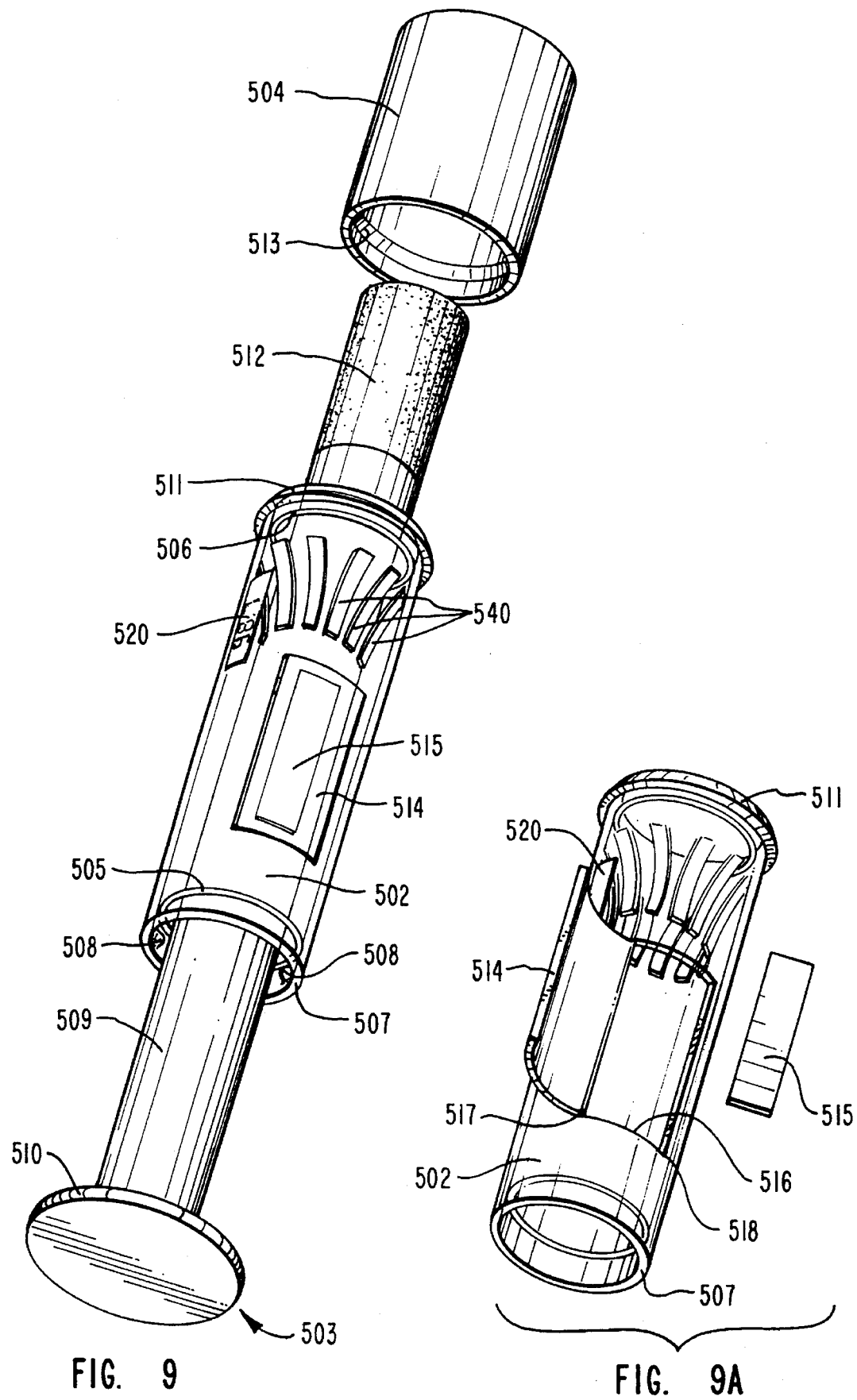
FIG. 9 depicts another preferred embodiment of the invention.
FIG. 9a depicts a window used in one preferred embodiment of the invention.

FIGS. 9 and 9a depict an alternative preferred embodiment of the fluid specimen collection and testing apparatus 1. It includes as major components a plunger 503, barrel 502 and sealable cap 504. The plunger consists of a plunger handle 510 at the proximal end of the plunger, plunger shaft 509, and o-rings or seals 506 and hydrophilic foam 512 at the distal end of the plunger. The barrel 502 consists of a barrel base 502 at its proximal end, temperature sensor 520, sealable hinged transparent window 514 capable of accepting reagent strips 515, a sealable one-way snap-lip 511 at the proximal barrel end, and in its interior a one-way plunger valve 540 consisting of a number of flexible angled fingers to provide a backstop for compression of absorbent material 512 by plunger 503. The cap 504 includes a sealable snap-lip 513 for mounting to the sealable barrel lip 511. The window 514 is mounted on a hinge 517 and includes a fluid-tight seal 518 around the window frame 516. The seal may be any rubber or other material capable of forming a seal both with the barrel 602 and the window 514 when the window is closed.

Use of the embodiment of the invention shown in FIGS. 3 and 3a is similar to the technique for using the embodiments shown in previous Figures. The user exposes the hydrophilic foam 512 to a fluid specimen to allow the foam 512 to absorb and retain specimen. The plunger 503 is then retracted into the barrel 502 and the cap 504 is mounted to and sealed against the sealable snap-lip 511. O-rings or seals 505 and 506 and the sealable snap-lip 511 prevent escape of specimen from the barrel 502. Medical personnel then place a reagent strip 515 into the window frame 516 and close the window utilizing fluid-tight seal 518 to prevent any leakage of specimen. The plunger 503 is then retracted further within the barrel 502 until the hydrophilic foam 512 passes the one-way plunger valve 540 and rests adjacent the window 514. The plunger 503 is then moved toward the distal end of the barrel 502 so that hydrophilic foam 512 is compressed against the one-way valve 540 and a quantity of fluid specimen is forced from the absorbent material thereby and permitted to contact with the reagent strip 515. Medical personnel time the exposure, observe color change in the reagent strip 515 and note test results. Release of the plunger allows hydrophilic foam 512 to resume its original shape and re-absorb the fluid specimen within the barrel 502. A new reagent strip 515 may then be inserted and another test on the specimen performed.

When testing is complete, the fluid specimen collection and testing apparatus 1 together with specimen are disposed of as a sealed unit. A plunger stop at the proximal end of the barrel 502 could be employed to prevent removal of plunger 503 from barrel 502 and hence prevent tampering. A non-openable snap-lip 511 and 513 could also be used to prevent access to specimen within the barrel 502 and hence prevent tampering. One-way valve fingers 540 could be any structure within the interior of the barrel 502 which would permit squeezing the hydrophilic foam 512 to extract a quantity of specimen therefrom. Temperature sensor 520 will indicate any substantial deviation from normal body temperature to indicate the introduction of a false specimen into the apparatus 1.

Plunger 503 movement causing compressing hydrophilic foam 51 against one-way valve fingers 540 to force a quantity of fluid specimen from the foam 512 and cause it to contact reagent strip 515 is considered a means for causing a quantity of fluid specimen to contact a reagent strip, a means for testing a fluid specimen, or a means for forcing a fluid specimen from the absorbent material. Reagent strip 515 alone is also considered a means for testing a fluid specimen.

The embodiments of the invention described herein as well as other embodiments of the invention provide a sealable fluid specimen collection and testing apparatus. Each embodiment described above includes features for easy collection of a specimen, namely the use of absorbent material to absorb or collect a quantity of specimen. The invention also includes features for sealing of specimen within the container, effectively isolating the specimen from personnel involved in its transport, handling, and testing. Thus, the specimen is isolated within a sealed container, preventing exit of specimen and providing a barrier between specimen and any personnel. The invention also includes features which permit testing of the specimen without the use of specialized laboratory equipment, such as in a doctor's office, in the home, in a police station, at a port of entry or on the job. Due to the sealing and containing features of the invention, there is minimal danger of contact between specimen and personnel performing the testing function.

Another advantage of the sealing and containing features of the invention is that after some initial testing, the invention with specimen still sealed in its interior, may be shipped to an off-site laboratory for further testing. For example, the embodiment of the invention depicted in FIG. 2 could be used to perform some testing of specimen, a luer cap placed onto the male luer lock, and the fluid collection and testing apparatus with specimen sealed within its interior shipped elsewhere for further testing.

The invention also provides a means for controlling the quantity of specimen absorbed for testing. The size and absorbency of the absorbent material used in the invention will determine the amount of specimen collected and may be selected accordingly. The quantity of specimen communicated to the specimen testing means may be controlled in the embodiments depicted in FIGS. 1, 2 and 3 by controlling the pressure placed on the absorbent material and hence the amount of specimen forced from the absorbent material. This is referred to as a means for controlling the quantity of fluid specimen communicated to specimen testing means. Each embodiment of the invention described herein includes a means for wringing or compressing the absorbent material in connection with the specimen communication function. Each embodiment of the invention also includes a means for viewing both specimen and reagent strip through a transparent enclosure or container by the use of clear film, clear plastic or a clear viewing window. And each embodiment of the invention serves as a means for collecting, confining, transmitting and testing a fluid specimen without exposing specimen to air, the environment or testing personnel.

Some embodiments of the invention provide a tamper-proof feature, so that once the specimen is sealed within its container, its integrity cannot be affected without easy detection by laboratory testing personnel. The description accompanying FIG. 1 refers to a one-way snap fitting which accomplishes this purpose. Use of permanent or non-resealable seals and the use of one-way ratchet mechanisms in joining parts could achieve this result as well. The inclusion of a temperature indicator strip in some embodiments of the invention to guard against the substitution of false specimens is a further safeguard provided by the invention.

Accurate timing of exposure of reagent to specimen is facilitated by the invention by keeping reagent and specimen physically separate until medical personnel articulate the invention to cause specimen to contact reagent. Specimen may be exposed to multiple reagents simultaneously by using reagent strips containing multiple reagents. Alternatively, the embodiment of the invention depicted in FIG. 3 would permit multiple reagent strips to be introduced into its testing chamber prior to introduction of a quantity of specimen into the testing chamber, also facilitating concurrent exposure of specimen to multiple reagents. Alternatively, several embodiments of the invention could be used to expose specimen to multiple reagents in sequence over time. For example, the embodiment of the invention depicted in FIG. 3 could be used to insert reagent strips one after another into the testing chamber, time exposure of reagent to specimen and record the test results. The invention conceals the method used for testing a biological fluid specimen from the patient providing the specimen. The embodiments depicted in FIGS. 1 and 3 would not even introduce the reagent strip in the presence of the specimen. The embodiment depicted in FIG. 2 introduces the reagent strip in the presence of the patient, but the reagent strip is concealed within the hollow straw and its purpose would not be obvious, so the likelihood of tampering attempts is reduced.

In each embodiment of the invention described herein, the materials and methods of manufacture used are those known in the art and could readily be adapted from syringe manufacturing materials and processes.

Any of the embodiments of the invention described above as well as other embodiments of the invention may be used not only for the collection and testing of a human urine specimen, but would be suitable for the collection and testing of a variety of biological fluid specimens. For example, in the veterinary setting, the invention could be used to collect urine specimens as urine is discharged from a subject animal or after discharge specimen could be collected from a container which captured the discharge. The invention could be used to collect specimens of saliva or the invention could be used to collect specimens of blood from an open wound or in conjunction with the use of a needle. The invention may also be used to collect specimens of fluids which are not biological in nature, such as water which is to be tested for hazardous effluents, or any liquid chemicals to be tested for any variety of purposes, such as for composition, purity/contamination or other reasons. In each application of the invention discussed herein as well as in other applications of the invention not yet contemplated, the advantages of the invention would be available. For example, the invention's ability to be used to collect, seal, contain, transport, test and dispose of a specimen with minimal risk of contact between specimen and personnel would be an advantage of the invention in every setting where it may be employed.

While the present description has included specific examples and embodiments, it will be understood that there is no intent to limit it by such disclosure, but rather, it is intended to cover all modifications and alternate constructions falling within the spirit and scope of the invention as defined in the appended claims.

We claim:

1. A fluid specimen collection and testing apparatus comprising:

(a) a sealable fluid-tight enclosure adapted to receive and seal within its interior a hollow straw with an absorbent material affixed thereto, and (b) said hollow straw having a longitudinal axis, a proximal end at one end of said longitudinal axis and a distal end at the opposite end of said longitudinal axis, said proximal and distal ends being closed to prevent entry of specimen, said straw comprising:

(i) a rigid sub-frame mounted to said proximal end of said hollow straw, (ii) said absorbent material capable of collecting the fluid specimen, said absorbent material being mounted to said sub-frame, and (iii) a reagent strip located within the interior of said hollow straw between said proximal end and said distal end, said reagent strip being in fluid isolation from said absorbent material;

wherein said proximal end is adapted to be grasped permitting deviation of said sub-frame from said longitudinal axis causing a fluid-permeable opening in said hollow straw, permitting fluid communication from said absorbent material to said reagent strip.

2. A device as recited in claim 1 wherein said fluid-tight enclosure is non-reopenable and non-resealable once sealed.

3. A device as recited in claim 1 wherein said reagent strip includes multiple patches of different reagents to test a fluid specimen with multiple reagents simultaneously.

4. A device as recited in claim 1 wherein said enclosure is constructed of transparent, flexible film.

5. A device as recited in claim 4 wherein said enclosure includes a temperature indicator.

6. A device as recited in claim 1 further comprising means of transporting, testing, and disposing of fluid specimen without exposing specimen to air, environment and personnel.

7. A fluid specimen collection and testing apparatus comprising:
(a) a sealable fluid-tight enclosure adapted to receive and seal within its interior a hollow straw with an absorbent material affixed thereto,
(b) said hollow straw having a proximal end and a distal end, said proximal and distal ends being closed to prevent entry of specimen, said straw having a rigid sub-frame mounted to said proximal end, said absorbent material capable of collecting the fluid specimen mounted to said sub-frame, scoring located on said hollow straw adjacent said proximal end to create a fluid permeable opening in said hollow straw, a reagent strip within said hollow straw between said scoring and said proximal end being in fluid isolation from said absorbent material;

wherein said proximal end is adapted to be grasped permitting deviation of said sub-frame from the longitudinal axis of said hollow straw causes said fluid-permeable opening in said hollow straw at said scoring, permitting fluid communication between said reagent strip and said absorbent material.

8. A device as recited in claim 7 wherein said fluid-tight enclosure is non-reopenable and non-resealable once sealed.

9. A device as recited in claim 7 wherein said reagent strip includes multiple patches of different reagents to test a fluid specimen with multiple reagents simultaneously.

10. A device as recited in claim 7 wherein said enclosure is constructed of transparent, flexible film.

11. A device as recited in claim 10 wherein said enclosure includes a temperature indicator.

12. A device as recited in claim 7 further comprising means of transporting, testing, and disposing of fluid specimen without exposing specimen to air, environment and personnel.

* * * * *